(12) United States Patent
Uchihashi et al.

(10) Patent No.: US 7,943,383 B2
(45) Date of Patent: May 17, 2011

(54) APPARATUS AND METHOD FOR AUTOMATICALLY DETERMINING THE VALIDITY OF WHITE BLOOD SAMPLE MEASUREMENTS BASED ON THE CHARACTERISTICS OF OPTICAL SCATTERING DATA

(75) Inventors: Kinya Uchihashi, Kakogawa (JP); Yoshiro Ikeuchi, Kobe (JP); Noriyuki Narisada, Akashi (JP)

(73) Assignee: Sysmex Corporation, Kobe-Shi (JP)

( * ) Notice: Subject to any disclaimer, the term of this patent is extended or adjusted under 35 U.S.C. 154(b) by 563 days.

(21) Appl. No.: 11/824,002

(22) Filed: Jun. 28, 2007

(65) Prior Publication Data

US 2008/0041140 A1    Feb. 21, 2008

(30) Foreign Application Priority Data

Jun. 29, 2006    (JP) .................... 2006-180196

(51) Int. Cl.
*G01N 33/49* (2006.01)
(52) U.S. Cl. ............ 436/63; 436/8; 436/10; 436/164; 436/172; 422/73; 422/82.05; 422/82.08; 422/82.09; 702/19; 702/21; 702/26; 702/29
(58) Field of Classification Search ............ 436/63, 436/10
See application file for complete search history.

(56) References Cited

U.S. PATENT DOCUMENTS

| | | |
|---|---|---|
| 6,979,570 B2 | 12/2005 | Narisada |
| 2005/0202400 A1 | 9/2005 | Tsuji et al. |

FOREIGN PATENT DOCUMENTS

| | | |
|---|---|---|
| EP | 1542008 A | 6/2005 |
| JP | 2002-148261 A | 5/2002 |

OTHER PUBLICATIONS

Mori, Yusuke; et al. "Automation of bone marrow aspirate examination using the XE-2100 automated hematology analyzer." Cytometry Part B (Clinical Cytometry) 58B (2003) p. 25-31.*
O'Neil, Patrick; et al. "Performance evaluation of the complete blood count and white blood cell differential parameters on the AcT 5diff hematology analyzer." Laboratory Hematology 7 (2001) p. 116-124.*
Briggs, C.; et al. "Performance evaluations of a new compact hematology analyzer, the Sysmex pocH-100i." Laboratory Hematology 9 (2003) p. 225-233.*
European Search Report for European Application No. 07012709.7, dated Jun. 5, 2009, 2 pages.

* cited by examiner

*Primary Examiner* — Yelena G Gakh
*Assistant Examiner* — Christopher A Hixson
(74) *Attorney, Agent, or Firm* — Brinks Hofer Gilson & Lione

(57) ABSTRACT

A blood analyzer configured to prevent an abnormal number of white blood cells caused by lipid particles or red blood cells of poor hemolysis from being output. The blood analyzer includes a system for obtaining a first white blood cell number and a system for obtaining a second white blood cell number. The analyzer also includes an output device for outputting the second white blood cell number, and a system for determining whether the second white blood cell number is abnormal. The output device is configured to output the first white blood cell number when the second white blood cell number has been determined to be abnormal.

17 Claims, 19 Drawing Sheets

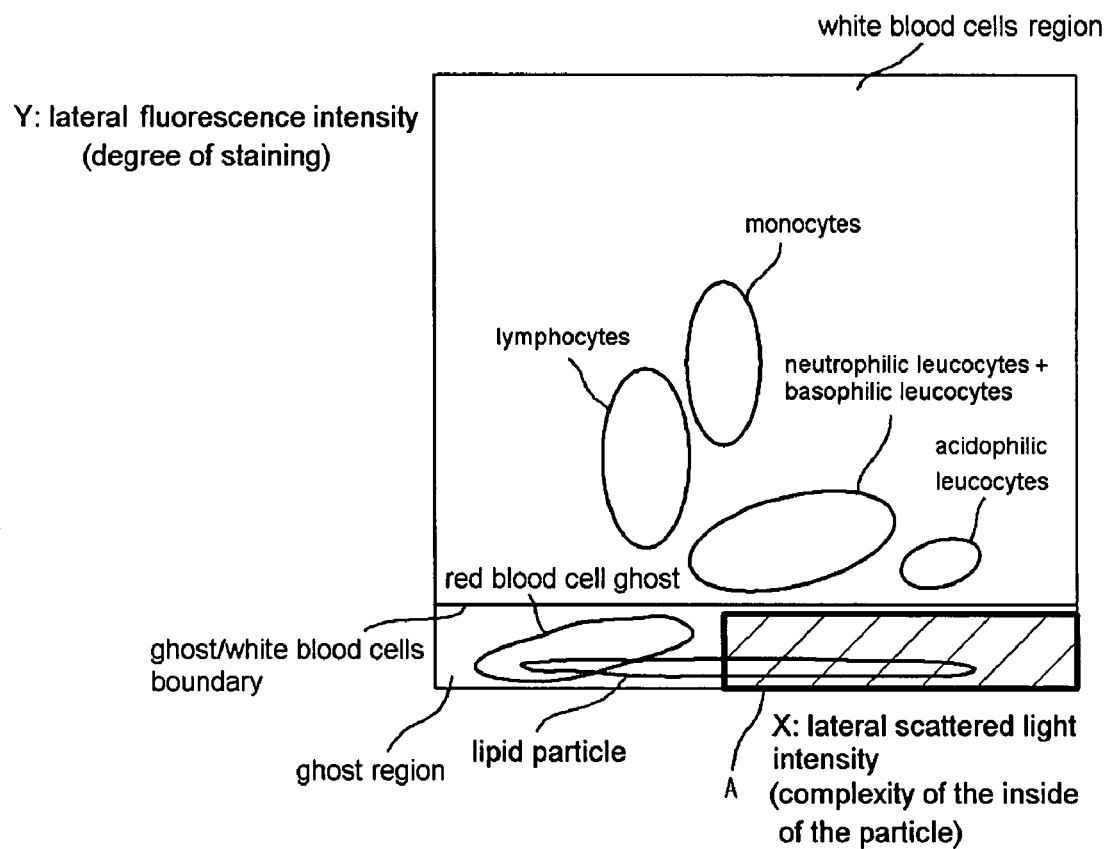

Y: lateral fluorescence light intensity

DIFF

X: lateral scattered light intensity

APPARATUS AND METHOD FOR AUTOMATICALLY DETERMINING THE VALIDITY OF WHITE BLOOD SAMPLE MEASUREMENTS BASED ON THE CHARACTERISTICS OF OPTICAL SCATTERING DATA

RELATED APPLICATIONS

This application claims priority under 35 U.S.C. §119 to Japanese Patent Application No. JP2006-180196 filed Jun. 29, 2006, the entire content of which is hereby incorporated by reference.

FIELD OF THE INVENTION

The present invention relates to an analyzer such as blood analyzer and a method for analyzing blood.

BACKGROUND

A blood analyzer aspirates blood in a blood collection tube, mixes the aspirated blood sample with a reagent such as hemolyzing agent to prepare a measurement sample. The blood analyzer then measures the measurement sample, analyzes measurement data obtained by the measurement, and acquires an analysis result, such as the number of blood cells.

For instance, when detecting the number of white blood cells through a method referred to as flow cytometry, a blood sample is sent to an optical detector (flow cell) after red blood cells in the blood sample are hemolyzed by a hemolyzing agent and the blood sample is diluted.

In the optical detector, laser light is irradiated on the blood cells. The blood analyzer prepares a two dimensional distribution chart (scattergram) of the particles based on the forward scattered light and the lateral scattered light obtained by the irradiation with the laser light.

U.S. Pat. No. 6,979,570 discloses a particle analyzer as described above. In the particle analyzer disclosed in U.S. Pat. No. 6,979,570, the white blood cells are classified based on the scattergram, and the number of white blood cells is calculated.

The inventors found the following problems in detecting the number of particles in the analyzer. When lipid particles in the blood increase through administration of lipid emulsion to the patient, as shown in FIG. 12, the lipid particles appear on the scattergram. Therefore, when the number of white bloods cells is detected based on the scattergram, a greater number of white blood cells than the actual number of white blood cells is detected due to the presence of lipid particles, and the number of reported white blood cells is a pseudo-high value. FIG. 12 is obtained by the measurement performed by the analyzer of the present embodiment.

If the membrane resistance of red blood cells is high, hemolysis is sometimes poor where the red blood cells are not sufficiently hemolyzed by the hemolyzing agent. The particles of poor hemolysis also appear on the scattergram as measurement data, as shown in FIGS. 13 and 14. Therefore, if the number of white blood cells is detected based on such a scattergram, a greater number of white blood cells than the actual number of white blood cells is detected due to the presence of particles of poor hemolysis, and the number of reported white blood cells is a pseudo-high value. FIGS. 13 and 14 are also obtained by the measurement performed by the analyzer of the present embodiment.

SUMMARY

A first aspect of the present invention is an analyzer for analyzing a blood sample, comprising: first white blood cell number obtaining means for performing a first classification related to white blood cells contained in a blood sample and obtaining a number of the white blood cells contained in the blood sample, based on first measurement data obtained by measuring a measurement sample which contains the blood sample; second white blood cell number obtaining means for performing a second classification related to white blood cells contained in the blood sample and obtaining a number of the white blood cells contained in the blood sample, based on second measurement data obtained by measuring a measurement sample which contains the blood sample; output means for outputting the number of the white blood cells obtained by the second white blood cell number obtaining means, and determining means for determining whether the number of the white blood cells obtained by the second white blood cell number obtaining means is abnormal, based on at least one of the first measurement data and the second measurement data, wherein the output means is configured to output the number of the white blood cells obtained by the first white blood cell number obtaining means when the determining means determines that the number of the white blood cells obtained by the second white blood cell number obtaining means is abnormal.

A second aspect of the present invention is an analyzer for analyzing a blood sample, comprising: first white blood cell number obtaining means for performing a first classification related to white blood cells contained in a blood sample and obtaining a number of the white blood cells contained in the blood sample, based on first measurement data obtained by measuring a measurement sample which contains the blood sample; second white blood cell number obtaining means for performing a second classification related to white blood cells contained in the blood sample and obtaining a number of the white blood cells contained in the blood sample, based on second measurement data obtained by measuring a measurement sample which contains the blood sample; selecting means for selecting one of the number of white blood cells obtained by the first white blood cell obtaining means and the number of white blood cells obtained by the second white blood cell obtaining means, based on at least one of the first measurement data and the second measurement data; and output means for outputting the number of the white blood cells selected by the selecting means.

A third aspect of the present invention is a method for analyzing a blood sample, comprising steps of: (a) performing a first classification related to white blood cells contained in a blood sample based on first measurement data obtained by measuring a measurement sample which contains the blood sample; (b) obtaining a number of the white blood cells contained in the blood sample based on a first classification result obtained in step (a); (c) performing a second classification related to white blood cells contained in the blood sample based on second measurement data obtained by measuring a measurement sample which contains the blood sample; (d) obtaining a number of the white blood cells contained in the blood sample based on a second classification result obtained in step (c); (e) determining whether the number of the white blood cells obtained in step (d) is abnormal, based on at least one of the first measurement data and the second measurement data; and (f) outputting the number of the white blood cells obtained in step (b) when the number of white blood cells obtained in step (d) is determined to be abnormal in step (e), and outputting the number of white blood cells obtained in step (d) when the number of white blood cells obtained in step (d) is determined not to be abnormal in step (e).

BRIEF DESCRIPTION OF THE DRAWINGS

FIG. 10(a) and FIG. 10(b) are explanatory views for detecting lipid particles on the scattergram;

DETAILED DESCRIPTION OF THE EMBODIMENT

The preferred embodiments of the present invention are described hereinafter based on the drawings.

Figure 1:
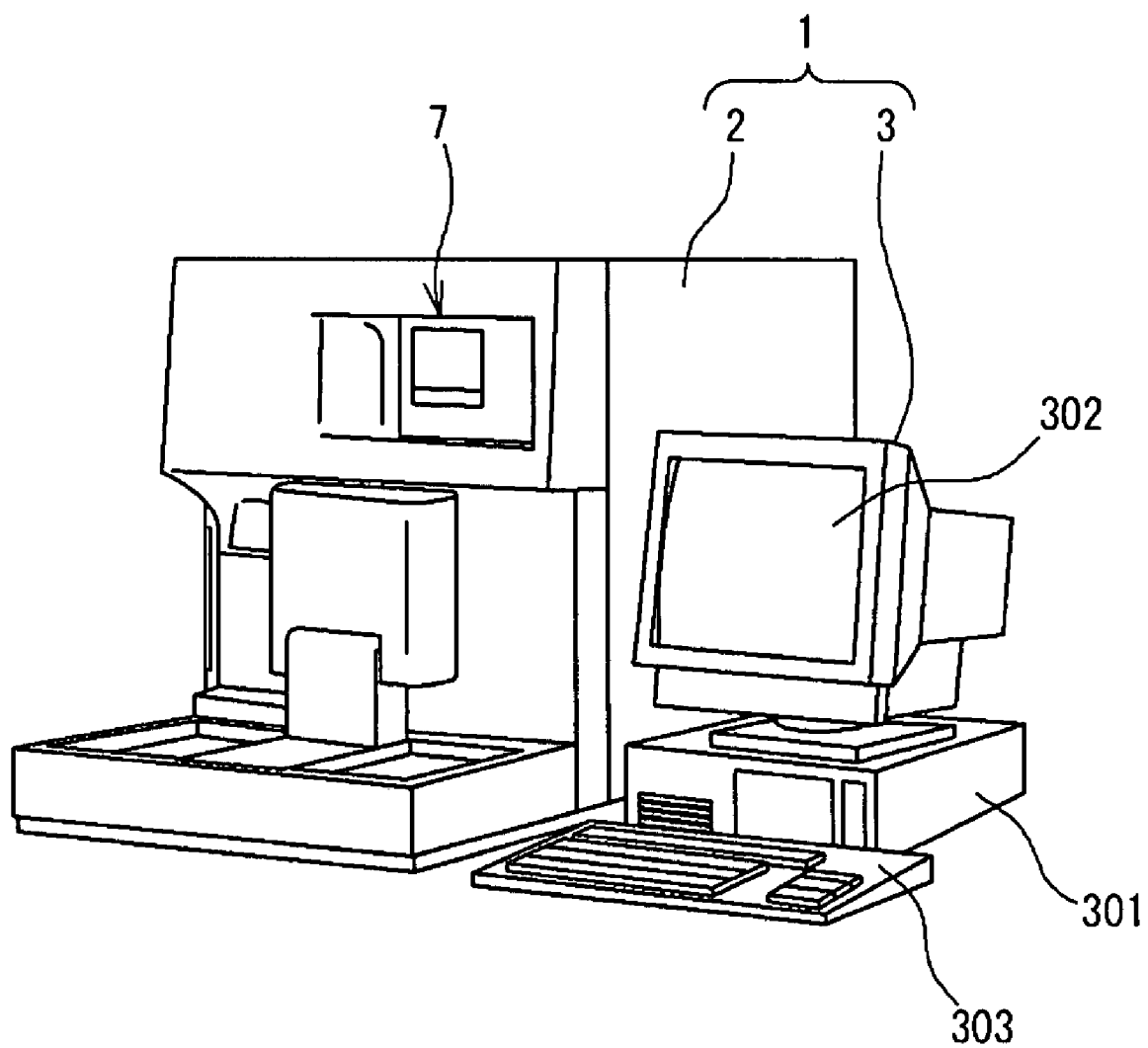
FIG. 1 is a perspective view showing a blood analyzer.

FIG. 1 shows a blood analyzer 1. The blood analyzer 1 is configured as a multiple automatic blood cell analyzer for performing a blood test, where measurement of the blood sample accommodated in a sample container (blood collection tube) is performed, and analysis of the measurement data is performed.

The analyzer 1 includes a measuring unit 2 having the function of measuring a blood sample, and a data processing unit 3 for analyzing measurement data which is output from the measuring unit 2 and obtaining an analysis result.

In FIG. 1, the measuring unit 2 and the data processing unit 3 are configured as separate devices, but may be configured as an integrated device.

The analyzer 1 can perform classification/counting of other blood cells in addition to classification/counting of white blood cells, but the following description is made mainly on the white blood cells.

Figure 2:
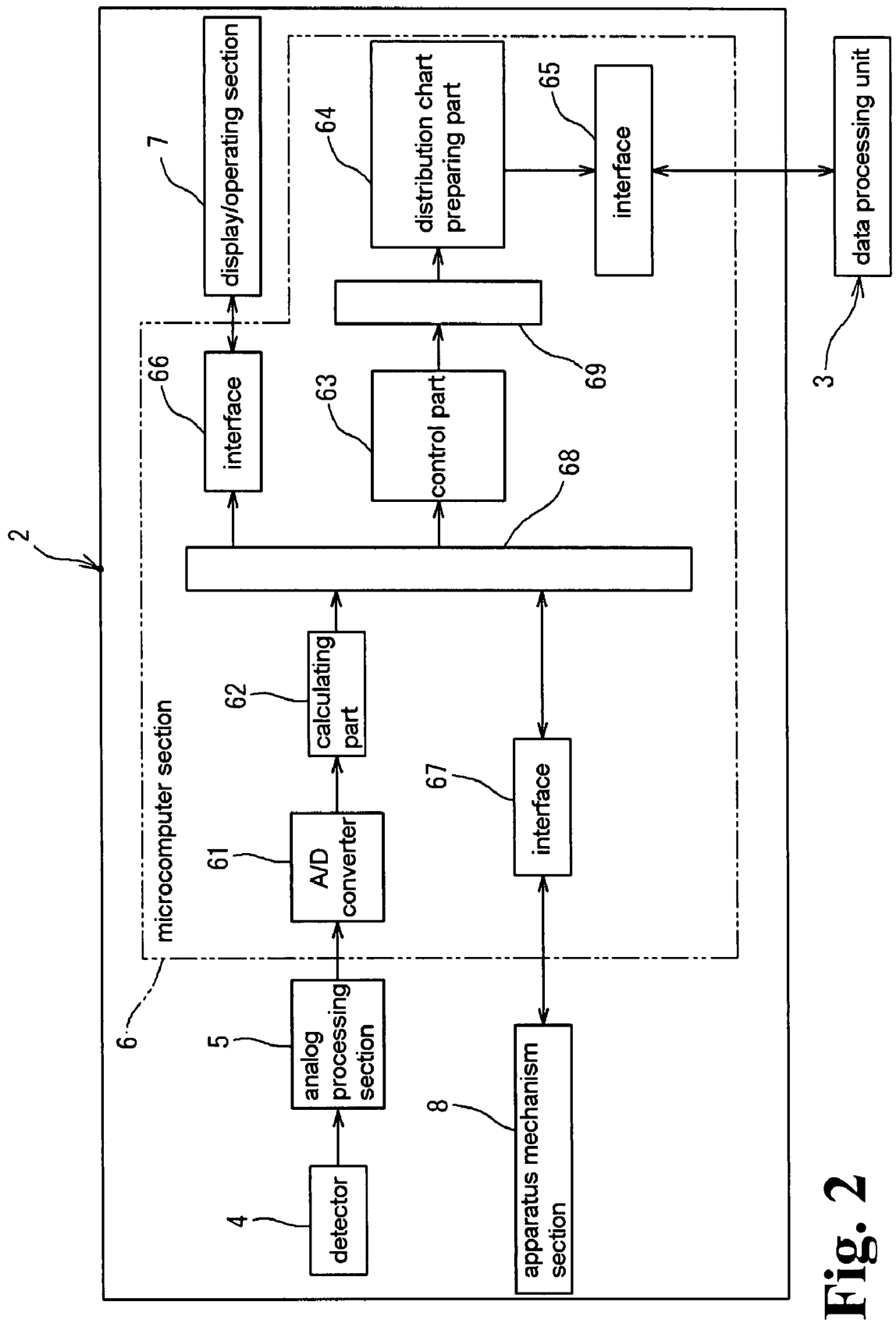
FIG. 2 is a functional block diagram of a measuring section.

FIG. 2 is a block diagram of the measuring unit 2 of the analyzer 1. As shown in FIG. 2, the measuring unit 2 includes a blood cell detector 4, an analog processing section 5 for the output of the detector 4, a microcomputer section 6, a display/operating section 7, and an apparatus mechanism section 8.

The detector 4 includes a white blood cell detector for detecting the white blood cells. In addition to the white blood cell detector, the detector 4 also includes an RBC/PLT detector for measuring the number of red blood cells and the number of platelets, an HGB detector for measuring the amount of hemoglobin in a blood, and an IMI detector for detecting immature leukocytes.

The white blood detector is configured as an optical detector, and specifically, is configured as a detector by flow cytometry method.

Cytometry relates to measuring physical property and chemical property of cells and other biological particles, and flow cytometry is a method of performing measurement by passing such particles into a narrow flow.

Figure 3:
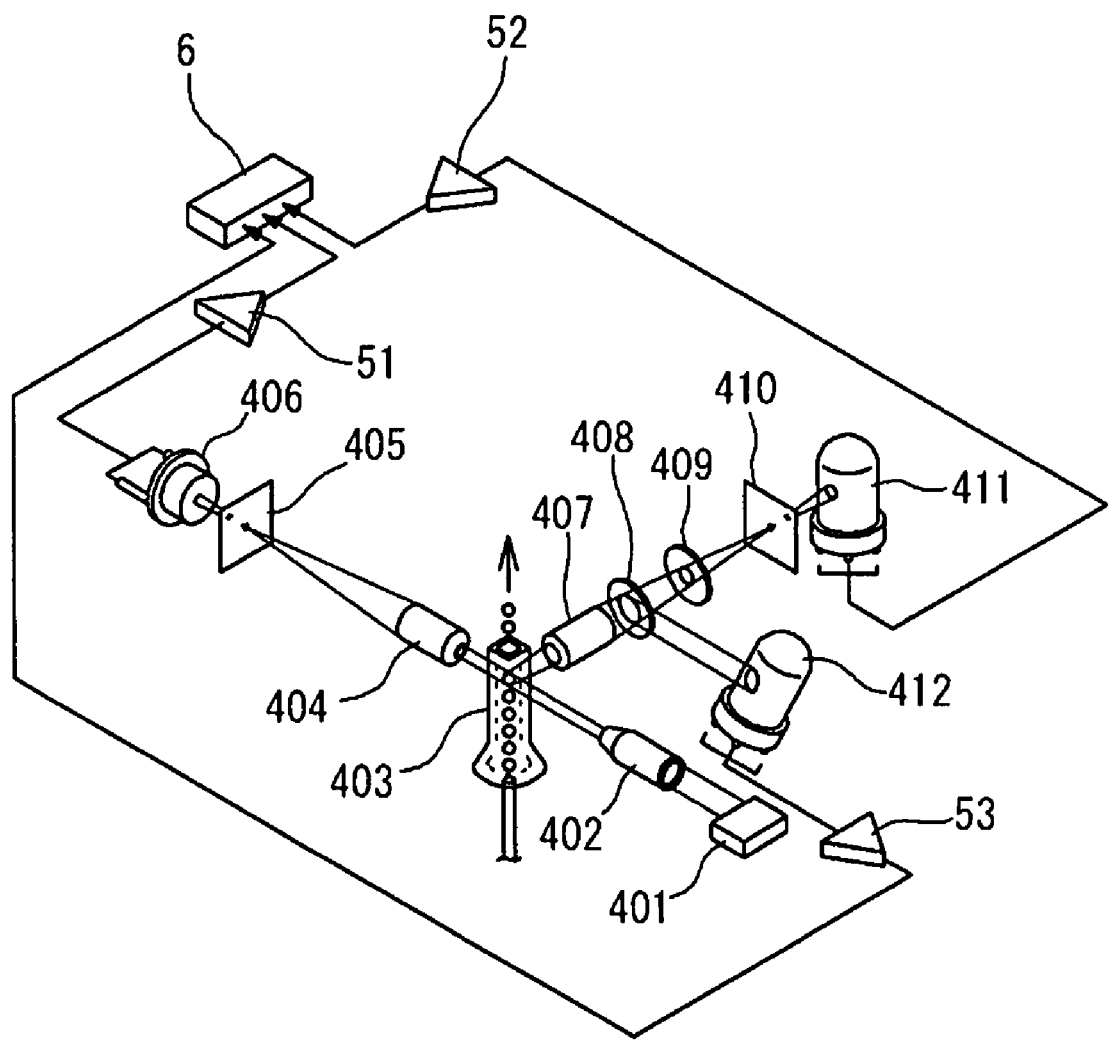
FIG. 3 is a configuration view of a detector.

FIG. 3 shows an optical system of the white blood cell detector. In the figure, a beam exit from a laser diode 401 is irradiated on the blood cells passing through a sheath flow cell 403 via an irradiation lens system 402.

In the white blood cell detector, the forward scattered light, lateral scattered light, and lateral fluorescence emitted from the blood cells in the sheath flow cell irradiated with the light are detected.

Light scattering is a phenomenon that occurs when particles such as blood cells exist as an obstacle in the advancing direction of the light and the light changes the advancing direction thereby. Information related to size and quality of material of the particles is obtained by detecting the scattered light. The forward scattered light is the scattered light emitted from the particle in a direction substantially the same as the advancing direction of the irradiated light. The information related to the size of the particle (blood cell) is obtained from the forward scattered light. The lateral scattered light is the scattered light emitted from the particle in a direction substantially perpendicular to the advancing direction of the irradiated light. The information from the inside of the particle is obtained from the lateral scattered light. When the laser light is irradiated on the blood cell particle, the lateral scattered light intensity depends on the complexity of the inside of the cell (shape, size, density of core and amount of granules). Therefore, the blood cells can be classified (discriminated) and the number of blood cells can be measured by using the specific property of the lateral scattered light intensity. In the present embodiment, a configuration of using the forward scattered light and the lateral scattered light as the scattered light has been described, but is not limited thereto, and scattered light of any angle with respect to the optical axis of the light transmitting through the sheath flow cell from the light source may be used as long as the scattered light signal which has features of the particle necessary for the analysis is obtained.

When the light is irradiated on fluorescent substances such as stained blood cells, light having a wavelength longer than the wavelength of the irradiated light is emitted. The fluorescence intensity is stronger if satisfactorily stained, and information related to the degree of stain of the blood cells can be obtained by measuring such fluorescence intensity. Therefore, measurement of the classification of the white blood cells and other measurements can be performed by the difference in (lateral) fluorescence intensity.

As shown in FIG. 3, the forward scattered light emitted from the blood cell (white blood cell) passing through the sheath flow cell 403 is received by a photodiode (forward scattered light receiving part) 406 via a light collecting lens 404 and a pin hole 405.

The lateral scattered light is received by a photo-multiplier (lateral scattered light receiving part) 411 via a light collecting lens 407, a dichroic mirror 408, an optical filter 409, and a pin hole 410.

The lateral fluorescence is received by a photo-multiplier (lateral fluorescence receiving part) 412 via the light collecting lens 407 and the dichroic mirror 408.

The light receiving signals output from each light receiving part 406, 411, and 412 are respectively subjected to analog processing such as amplification/waveform processing by the analog processing section 5 including amplifiers 51, 52, 53, and the like, and provided to the microcomputer section 6.

The microcomputer section 6 includes an A/D converter 61 for converting the light receiving signal provided from the analog processing section 5 to a digital signal. The output of the A/D converter 61 is provided to a calculating part 62 of the microcomputer section 6, and a calculation is performed for a predetermined process on the light receiving signal in the calculating part 62.

The microcomputer section 6 includes the control part 63 including a control processor and a memory for the control processor operation, and the distribution chart preparing part 64 including a processor and a memory for the chart preparing operation.

The control part 63 controls the apparatus mechanism section 8 including a sampler (not shown) for automatically supplying the blood collection tube, fluid system for preparing/measuring the sample, and the like, and also performs other controls.

The distribution chart preparing part 64 prepares a two dimensional scattergram (non-fractionated) based on the output of the detector 4. The distribution chart preparing part 64 is connected to the data processing unit 3 by way of an external interface 65, and transmits the measurement data such as the prepared scattergram to the data processing unit 3.

Furthermore, the microcomputer section 6 has an interface part 66 interposed between itself and the display/operating section 7, and an interface part 67 interposed between itself and the apparatus mechanism section 8.

The calculating part 62, the control part 63, and the interface parts 66, 67 are connected by way of a bus 68, and the control part 63 and the distribution chart preparing part 64 are connected by way of a bus 69.

The measuring unit 2 of the analyzer 1 of the present embodiment performs a first measurement (DIFF measurement) and a second measurement (WBC/BASO measurement) as the measurement of white blood cells on the same blood sample. The white blood cells are broadly classified into lymphocytes, monocytes, and granulocytes. Furthermore, the granulocytes are classified into neutrophilic leucocytes, basophilic leucocytes, and acidophilic leucocytes according to the stainability of the granules.

The first measurement (DIFF) measurement is a 4DIFF measurement of fractionate measuring the white blood cells into four groups, specifically, fractionate measuring into a lymphocytes group, a monocytes group, an acidophilic leucocytes group, as well as a neutrophilic leucocytes and basophilic leucocytes group, and counting the number of particles of each group.

Figure 4:
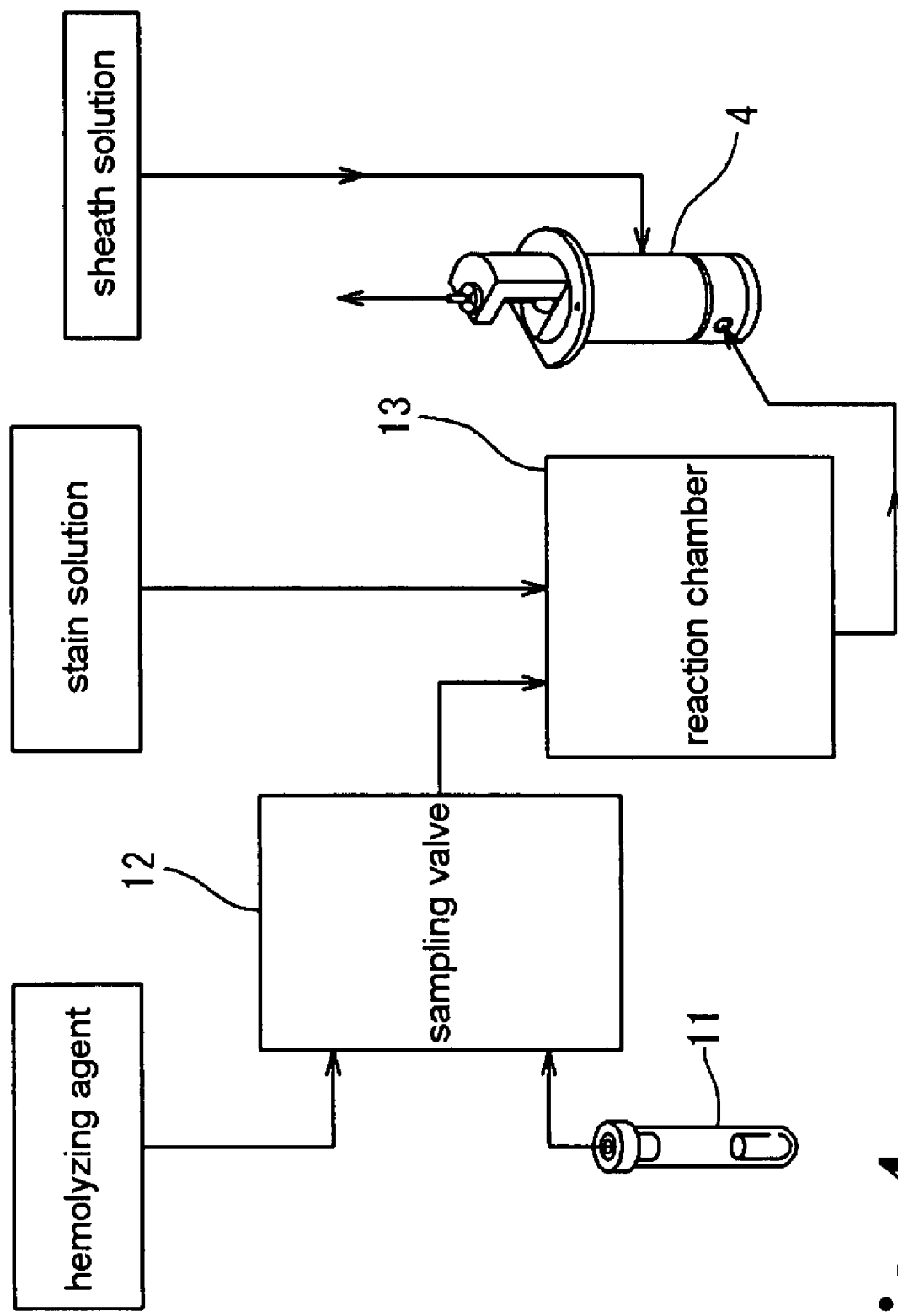
FIG. 4 is a view showing a flow of DIFF measurement.

FIG. 4 shows the flow of the 4DIFF measurement by the measuring unit 2. FIG. 4 shows the state of mixing a first reagent for first measurement (DIFF) into the blood sample and preparing a first measurement sample, and measuring the first measurement sample in the white blood cell detector.

In FIG. 4, the blood sample in the blood collection tube 11 is aspirated into a sampling valve 12 through an aspiration pipette (not shown). The blood sample which quantity is determined in the sampling valve 12 is diluted with a predetermined amount of hemolyzing agent (Stromatolyser 4DL manufactured by Sysmex Co.) serving as the first reagent, and supplied to a reaction chamber 13 as diluted sample. A predetermined amount of stain solution (Stromatolyser 4DS manufactured by Sysmex Co.) serving as another first reagent is supplied to the reaction chamber 13, and the diluted sample is further diluted. The diluted sample is reacted for a predetermined time in the reaction chamber 13 in this state, whereby the first measurement sample is obtained in which the red blood cells in the blood sample are hemolyzed and the white blood cells are stained.

The first measurement sample is sent to the white blood cell detector along with the sheath solution (Cell pack(II) manufactured by Sysmex Co.), and measured in the white blood cell detector using a flow cytometry method.

Figure 5:
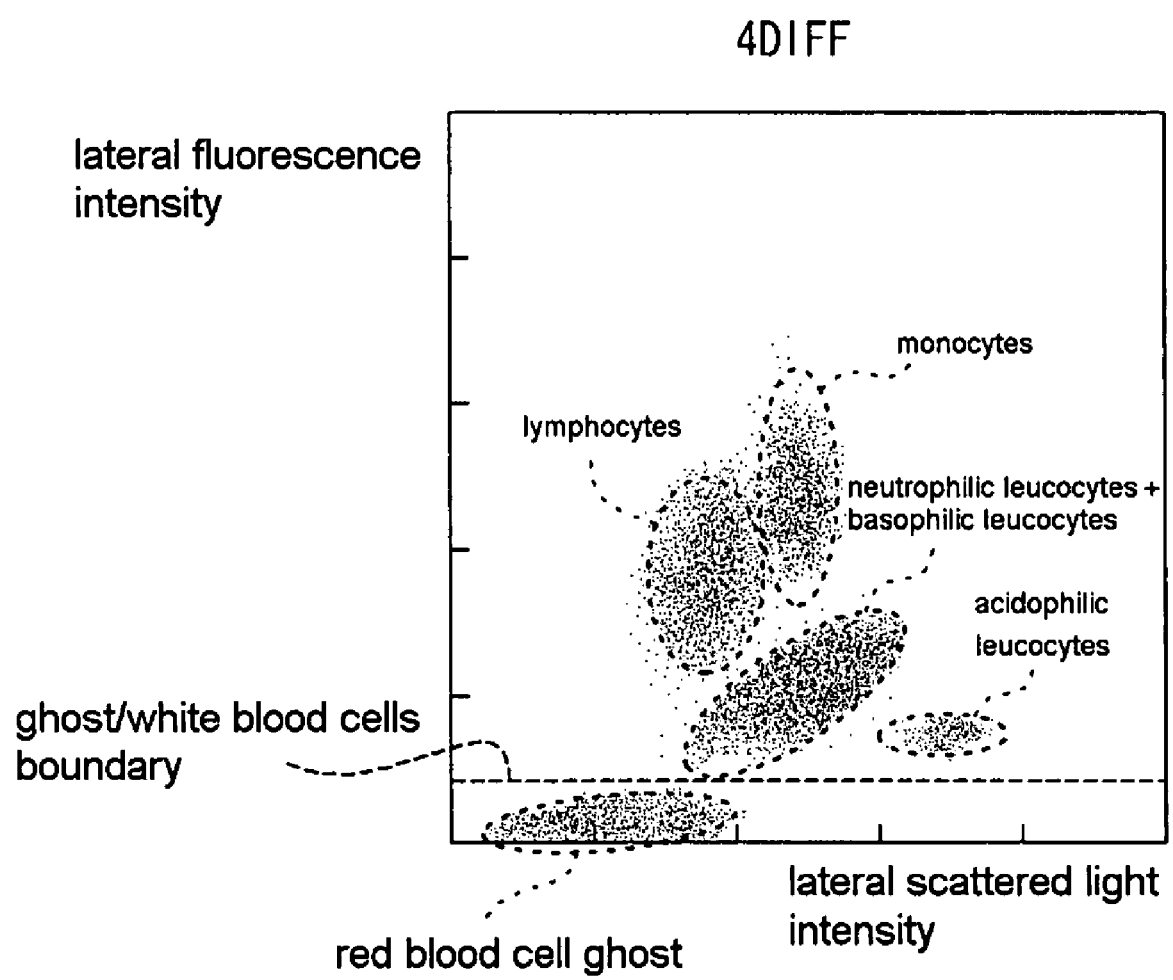
FIG. 5 shows a 4DIFF scattergram.

In the case of the first measurement, the distribution chart preparing part 64 prepares a two-dimensional scattergram (particle distribution chart) as shown in FIG. 5 as the first measurement data based on the signals of the lateral scattered light and lateral fluorescence of the light receiving signals output from the white blood cell detector. The signals of the lateral scattered light and the lateral fluorescence are referred to as herein as the first optical information.

The scattergram is drawn with the lateral scattered light intensity on the X axis and the lateral fluorescence intensity on the Y axis, and normally, "red blood cell ghost particle group", "lymphocytes particle group", "monocytes particle group", "neutrophilic leucocytes and basophilic leucocytes particle group" and "acidophilic leucocytes particle group" appear. The particle groups are recognized by analyzing (fractionate measuring) the scattergram by means of the data processing unit 3, and the first classification (DIFF classification) of the white blood cells is performed by the relevant analysis. The number of white blood cells is also counted in the analysis.

The hemolyzing agent (Stromatolyser 4DL manufactured by Sysmex Co.) serving as the first reagent has a relatively suppressed hemolyzing ability. Since the hemolyzing agent not only hemolyzes the red blood cells but also hemolyzes the white cells and contracts the same, classification of the white blood cells becomes difficult if the white blood cells are hemolyzed in excess, and thus hemolyzing is performed in a relatively gradual manner to suppress contraction of the white blood cells in DIFF in which the white blood cells are classified in a relatively fine manner.

The WBC/BASO measurement (second measurement) fractionate measures the blood cells in two groups of white blood cells (excluding basophilic leucocytes) group and the basophilic leucocytes in the blood sample, and the number of particles of each group is counted.

Figure 6:
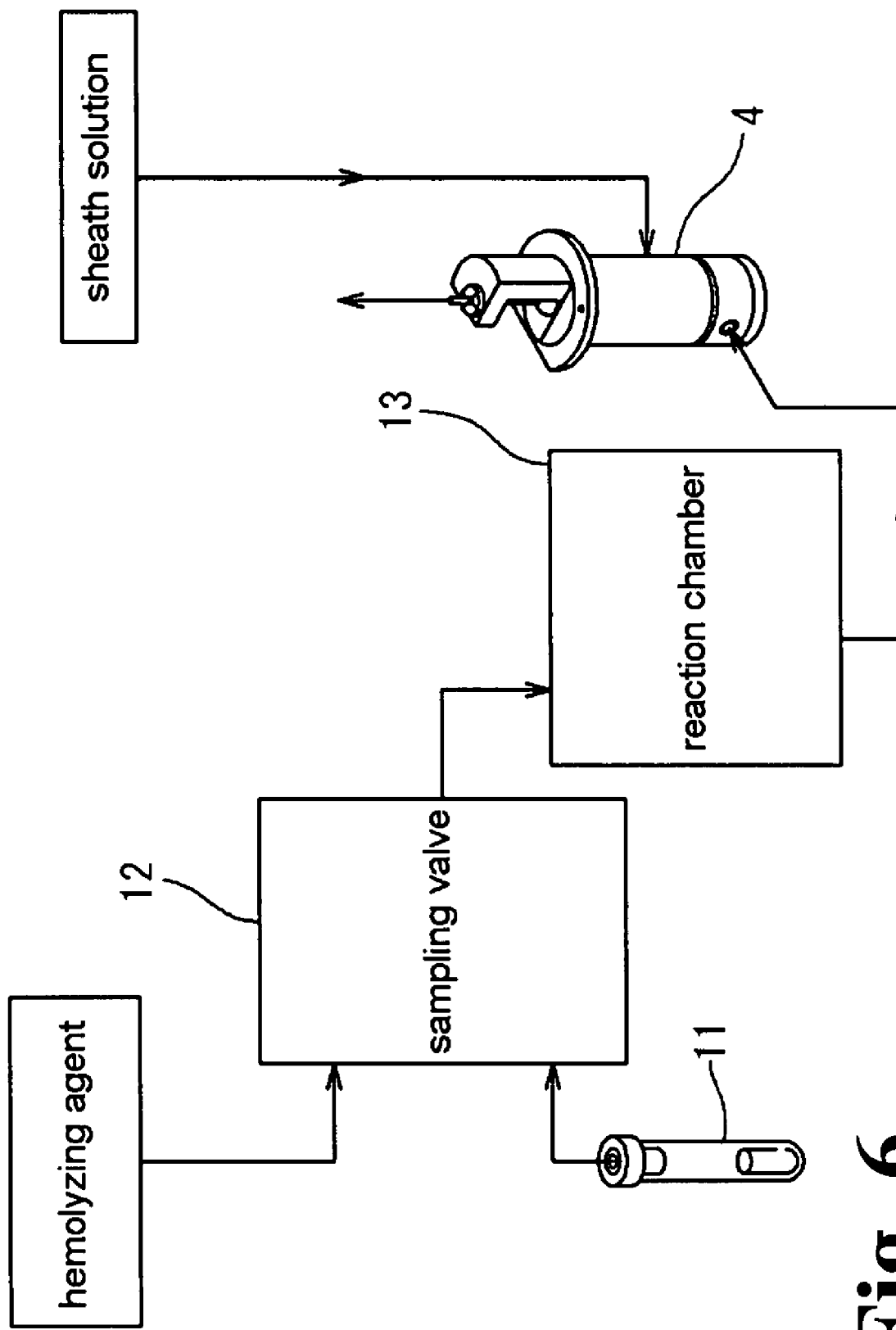
FIG. 6 is a view showing a flow of WBC/BASO measurement.

FIG. 6 shows the flow of WBC/BASO measurement by the analyzer 1. FIG. 6 shows a state of mixing a second reagent for second measurement (SBC/BASO) to the blood sample to prepare a second measurement sample, and measuring the second measurement sample in the white blood cell detector.

In FIG. 6, the blood sample in the blood collection tube 11 is aspirated into the sampling valve 12 through an aspiration pipette (not shown). The blood sample which quantity is determined in the sampling valve 12 is diluted with a predetermined amount of hemolyzing agent (Stromatolyser FB(II) manufactured by Sysmex Co.) serving as the second reagent, and conveyed to a reaction chamber 13 as diluted sample. The diluted sample is reacted for a predetermined time in the reaction chamber 13 in this state, whereby the second measurement sample in which the red blood cells in the blood sample are hemolyzed is obtained.

The second measurement sample is sent to the white blood cell detector along with the sheath solution (Cell pack(II) manufactured by Sysmex Co.), and measured in the white blood cell detector through the flow cytometry method.

Figure 7:
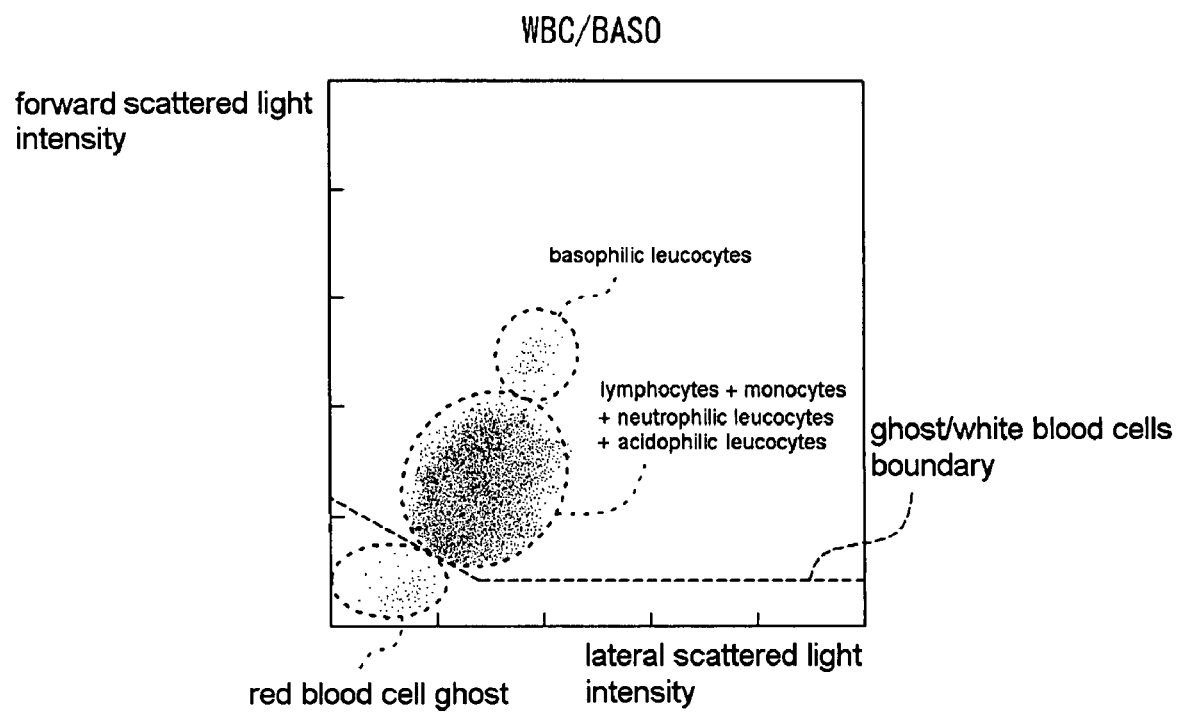
FIG. 7 shows a WBC/BASO scattergram.

In the case of the second measurement, the distribution chart preparing part 64 prepares a two-dimensional scattergram (particle distribution chart) shown in FIG. 7 as the second measurement data based on the signals of the lateral scattered light and forward scattered light of the light receiving signals output from the white blood cell detector. The signals of the lateral scattered light and the forward scattered light are referred to as herein as the second optical information.

The scattergram is drawn with the lateral scattered light intensity on the X axis and the forward scattered light intensity on the Y axis, and normally, "red blood cell ghost particle group", "basophilic leucocytes particle group", and "other white blood cells (lymphocytes, monocytes, neutrophilic leucocytes and acidophilic leucocytes) particle group" appear. The particle groups are recognized by analyzing (fractionate measuring) the scattergram by means of the data processing unit 3, and the second classification (WBC/BASO classification) of the white blood cells is performed by the relevant analysis. The number of white blood cells is also counted in the analysis.

The hemolyzing agent (Stromatolyser FB(II) 4DL manufactured by Sysmex Co.) serving as the second reagent has a relatively higher hemolyzing ability than the hemolyzing agent (Stromatolyser 4DL) serving as the first reagent. In the second measurement (WBC/BASO), since fine classification of the white blood cells is not performed, even if the white blood cells are also contracted to a certain extent by the hemolyzing agent, the number of white blood cells is reliably counted by reliably hemolyzing the red blood cells with the hemolyzing agent, and furthermore, the number of white blood cells can be detected while suppressing the influence of temporal change in the white blood cells after collecting blood.

Therefore, the analyzer 1 is able to perform measurement through two (a plurality of) measuring (fractionate measuring) methods on one particle (white blood cell), and two groups of (a plurality of) measurement data from the first measurement (non-fractionated scattergram) and the second measurement (non-fractionated scattergram) are obtained.

Figure 8:
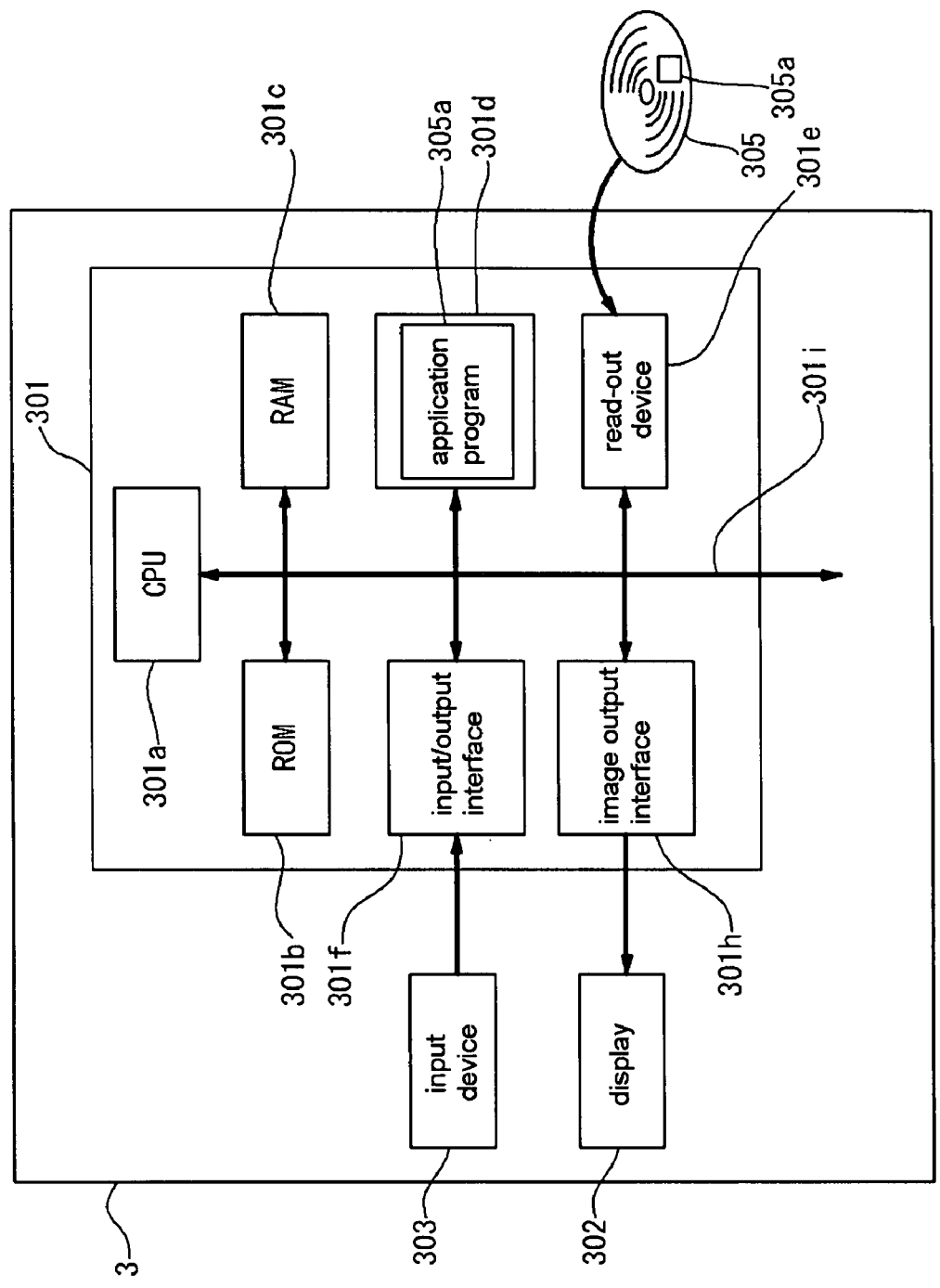
FIG. 8 is a functional block diagram of a data processing unit.

The microcomputer section 6 of the measuring unit 2 sends the first and second measurement data to the data processing unit 3. As shown in FIG. 8, the data processing unit 3 is configured as a computer, which is mainly configured by a main body 301, a display 302, and an input device 303. The main body 301 is mainly configured by CPU 301a, ROM 301b, RAM 301c, hard disc 301d, read-out device 301e, input/output interface 301f, and image output interface 301h, where the CPU 301a, ROM 301b, RAM 301c, hard disc 301d, read-out device 301e, input/output interface 301f, and image output interface 301h are data communicatably connected by a bus 301i.

The CPU 301a is capable of executing the computer program stored in the ROM 301b and the computer program loaded in the RAM 301c. When the CPU 301a executes an application program 305a, to be hereinafter described, each functional block to be hereinafter described is realized, and the computer functions as the data processing unit 3.

The ROM 301b is configured by mask ROM, PROM, EPROM, EEPROM, and the like, and is recorded with the computer program to be executed by the CPU 301a, data used for the same, and the like.

The RAM 301c is configured by SRAM, DRAM, or the like. The RAM 301c is used to read out the computer program recorded on the ROM 301b and the hard disc 301d. When executing such computer program, the RAM 301c is used as a work region of the CPU 301a.

The hard disc 301d is installed with various computer programs for the CPU 301a to execute such as operating system and application program, and data used in execution of the computer programs. The application program 305a to be hereinafter described is also installed in the hard disc 301d.

The read-out device 301e is configured by flexible disc drive, CD-ROM drive, DVD-ROM, or the like, and reads computer program or data recorded on a portable recording medium 305. The application program 350a for the computer to realize a predetermined function is stored in the portable recording medium 305, and the computer serving as the data processing unit 3 is able to read out the application program 305a from the portable recording medium 305 and install the application program 305a in the hard disc 301d.

The application program 305a is not only provided by the portable recording medium 305, and may be provided through the electric telecommunication line from the external equipment communicatably connected to the data processing unit 3 by the electric telecommunication line (wired or wireless). For instance, the application program 305a may be stored in the hard disc of the server computer on the Internet, and the data processing unit 3 may access the server computer, download the computer program and install the same in the hard disc 301d.

The operating system that provides graphical user interface environment such as Windows (Registered trademark) manufactured and sold by US Microsoft Co., Ltd. is installed in the hard disc 301d. In the following description, the application program 305a according to the present embodiment operates on the operating system.

The input/output interface 301f is configured by serial interface such as USB, IEEE1394, RS-232C; parallel interface such as SCSI, IDE, IEEE1284; analog interface including D/A converter, A/D converter and the like. The input device 303 including keyboard and mouse is connected to the input/output interface 301f, so that the data can be input to the data processing unit 3 when the user uses the input device 303.

The image output interface 301h is connected to the display 302 configured by LCD, CRT, or the like, and outputs a picture signal corresponding to the image data provided from the CPU 301a to the display 302. The display 302 displays the image (screen) according to the input picture signal.

Figure 9:
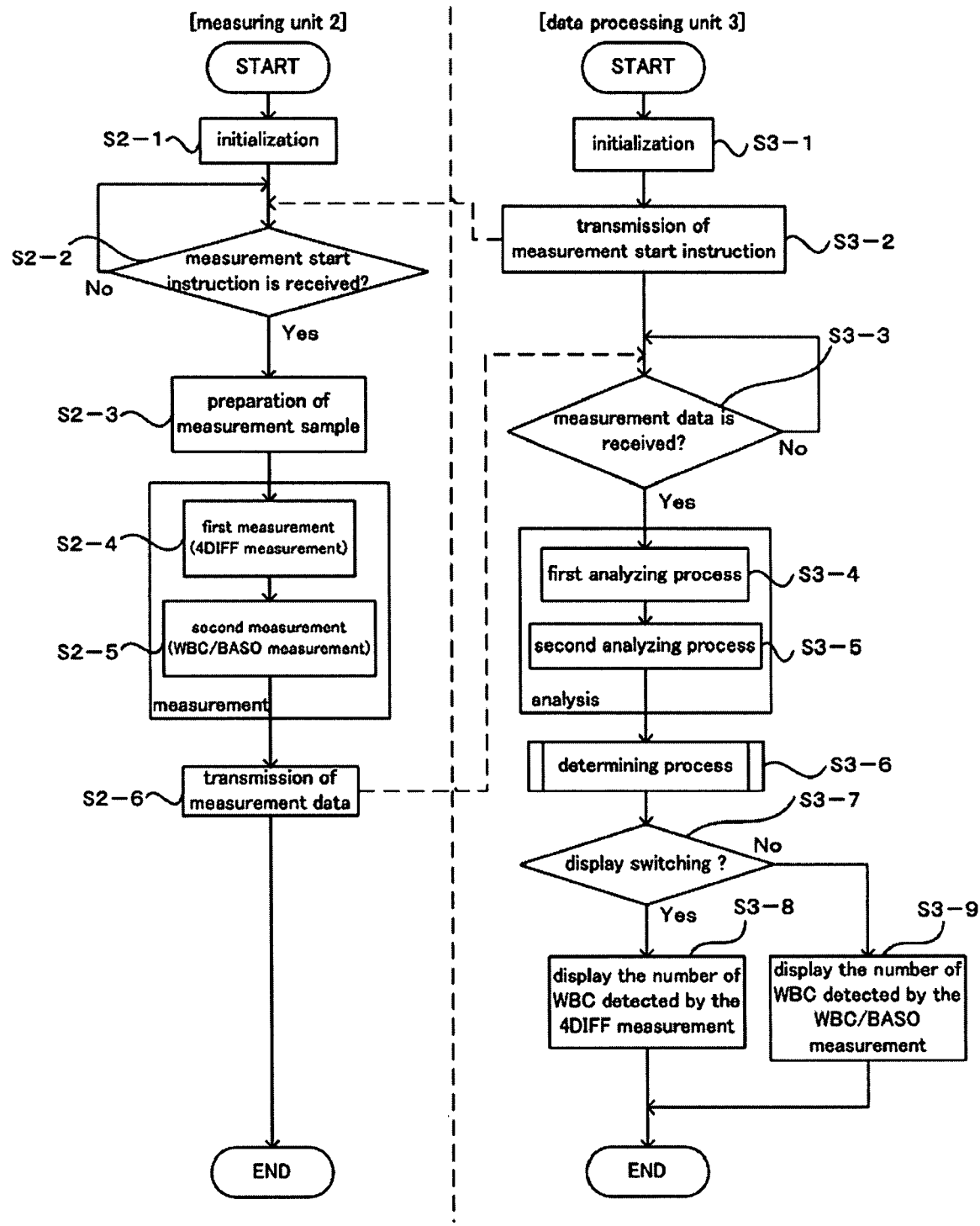
FIG. 9 is a flowchart of measurement and analysis.

FIG. 9 shows the process flow by the data processing unit 3 and the process flow of the measuring unit 2 associated therewith by the application program (data processing program). First, when the power of the measuring unit 2 and the data processing unit 3 is turned ON by the operation of the user, initialization of each mechanism section of the measuring unit 2, and initialization of the computer program etc. stored in the data processing unit 3 are performed (step S2-1, S3-1).

Subsequently, a measurement start instruction is transmitted from the data processing unit 3 side to the measuring unit 2 side through the operation etc. of the user (step S3-2), and the measuring unit 2 determines whether or not the measurement start instruction is received (step S2-2).

When determined that the measurement start instruction is received, the measuring unit 2 prepares the first and second measurement samples (step S2-3). The preparation of the first and second measurement samples in step S2-3 is performed in parallel.

The first measurement (4DIFF measurement) (step S2-4), and the second measurement (WBC/BASO measurement) (step S2-5) are sequentially performed by the white blood cell measuring part of the measuring unit 2.

The measuring unit 2 then transmits the measurement data (first and second measurement data) acquired in the first and second measurements to the data processing unit 3 (step S2-6).

The data processing unit 3 determines whether or not the first and second measurement data are received from the measuring unit 2 (step S3-3), and executes the analyzing process described below when determined that the measurement data are received.

[Analyzing Process]

The data processing unit 3 executes the analyzing process such as fractionate processing for classifying the white blood cells on the first and second measurement data (step S3-4, S3-5). A boundary process for distinguishing between the white blood cells and the ghost such as red blood cells is also performed in the analyzing process.

(Boundary Process)

In the first analysis of the DIFF measurement (first measurement) result, a predetermined fluorescence intensity for distinguishing the white blood cells (lymphocytes, monocytes, neutrophilic leucocytes+basophilic leucocytes, acidophilic leucocytes) and the red blood cell ghost is set as the "ghost/white blood cells (target particle) boundary" on the DIFF scattergram, as shown in FIG. 5. In the boundary process based on the DIFF measurement data, the particles in the range (white blood cells range) in which the fluorescence intensity (degree of staining) is larger than the ghost/white blood cells boundary are recognized as the white blood cells (target particles), and the particles in the range (ghost range) in which the fluorescence intensity is lower than the boundary are recognized as the ghost.

In the second analysis on the WBC/BASO measurement (second measurement), the "ghost/white blood cells (target particles) boundary" is set on the WBC scattergram as shown in FIG. 7. This boundary is downside in the range in which the lateral scattered light intensity is low where the forward scattered light intensity becomes smaller as the lateral scattered light intensity becomes larger, and the forward scattered light is constant in the range in which the lateral scattered light intensity is high. In the boundary process based on the WBC/BASO measurement data, the particles in the range (white blood cells range) in which the forward scattered light intensity (size of particles) is larger than the ghost/white blood cells boundary are recognized as the white blood cells (target particles), and the particles in the range (ghost range) in which the forward scattered light intensity (size of particles) is lower than the boundary are recognized as the ghost.

(Fractionating Process)

In the fractionating process, the particles recognized as the white blood cells in the boundary process are further classified into a plurality of classes of white blood cells by the recognition (fractionation) of the particle groups (clusters). That is, the white blood cells are fractionated/classified into four clusters in the first analyzing process (DIFF analyzing process).

The particles belonging to the four clusters are ultimately recognized as the white blood cells. In the second analyzing process (WBC/BASO analyzing process), the white blood cells are fractionated/classified into two clusters, and the particles belonging to the two clusters are ultimately recognized as the white blood cells. The number of white blood cells detected by the DIFF analyzing process and the number of white blood cells detected by the WBC/BASO analyzing process are respectively obtained from the number of particles recognized as the white blood cells in each scattergram by the fractionating process.

The boundary for distinguishing between the cluster and the other region on the scattergram is generated in each fractionated cluster. The particles present within the boundary are recognized as the particles belonging to the cluster.

When the fractionating process is performed, the cluster of the white blood cells sometimes extends to the ghost range or the cluster of the red blood cell ghost sometimes extends to the white blood cells range.

(Classification of the White Blood Cells into Five Classes)

The data processing section 3 classifies the white blood cells of the blood sample into five classes based on the result (first classification result) of classifying the white blood cells into four classes by the first analyzing process and the result of classifying the white blood cells into two classes by the second analyzing process. Specifically, the number of neutrophilic leucocytes and the number of basophilic leucocytes are respectively calculated from the "neutrophilic leucocytes+basophilic leucocytes group" obtained by the first analyzing process and the "basophilic leucocytes group" obtained by the second analyzing process. Thus, the white blood cells are classified into five classes (lymphocytes, monocytes, neutrophilic leucocytes, basophilic leucocytes, acidophilic leucocytes) based on each number of blood cells of the other three white blood cells group obtained by the first analyzing process to obtain the number of white blood cells of each classifying item.

[Determining Process]

The data processing unit 3 performs the following determining process based on the first measurement data and the second measurement data, and if necessary, based on the first analysis result and the second analysis result (step S3-6).

[Abnormality Determining Process of Number of White Blood Cells (Number of Particles)]

Figure 15:
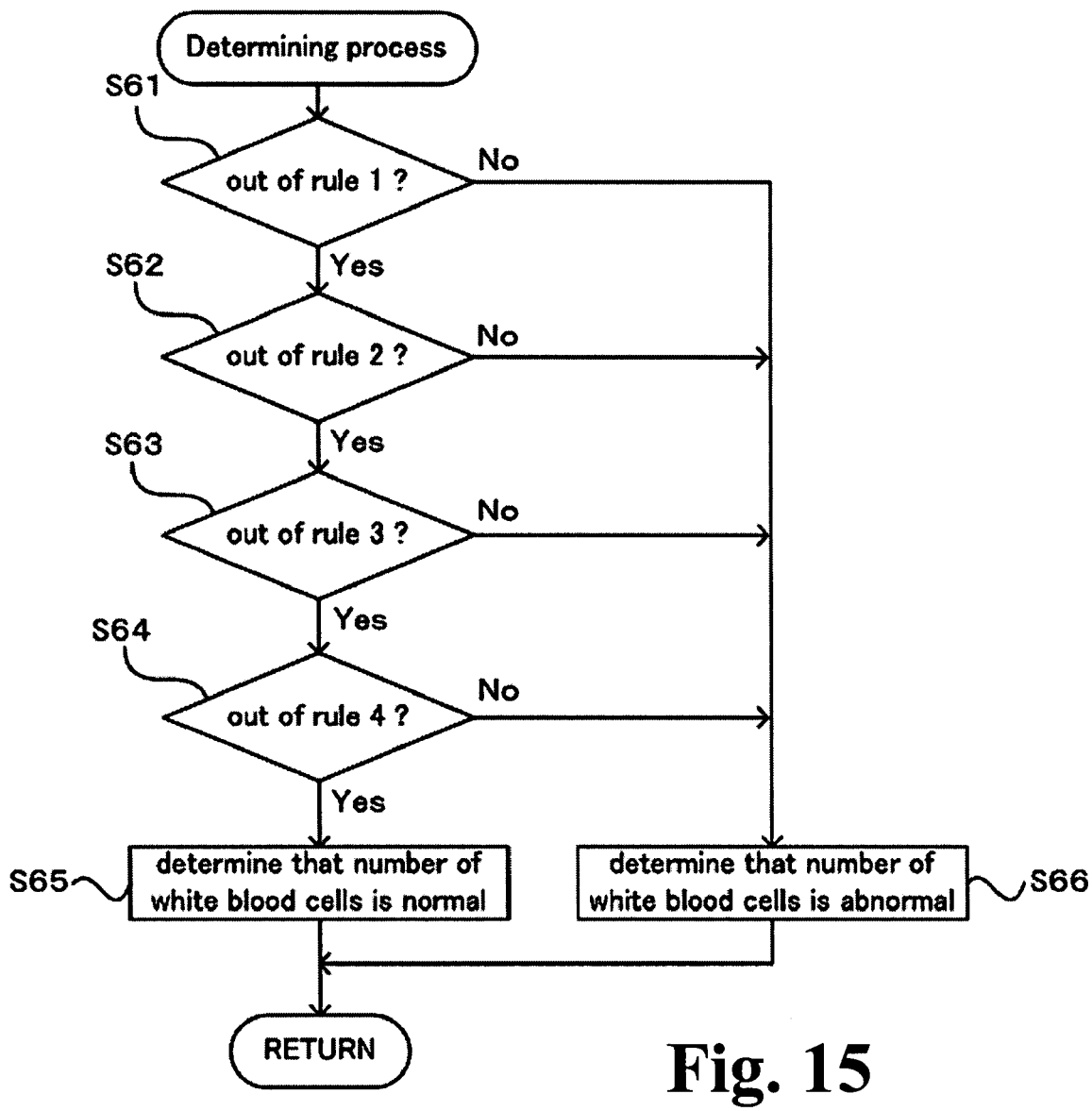
FIG. 15 is a flowchart of a determining process performed by the data processing unit.

As shown in FIG. 15, the data processing unit 3 first determines whether the first measurement data is out of rule 1 hereinafter described (step S61). If determined that the first measurement data is out of rule 1, the data processing unit 3 determines whether the second measurement data is out of rule 2 hereinafter described (step S62). If the second measurement data is determined to be out of rule 2, the data processing unit 3 determines whether the second measurement data is out of rule 3 hereinafter described (Step S63). If determined that the second measurement data is out of rule 3, the data processing unit 3 determines whether the second measurement data is out of rule 4 hereinafter described (step S64). If determined that the first measurement data and the second measurement data are out of all rules 1 to 4 through steps S61 to 64, the data processing unit 3 determines that the number of white blood cells detected based on the second measurement (WBC/BASO measurement) is normal (step S65). If determined that the first measurement data and the second measurement data correspond to one of the rules 1 to 4 through steps S61 to 64, the data processing unit 3 determines that the number of white blood cells detected based on the second measurement (WBC/BASO measurement) result contain number of particles other than the white blood cells, and thus is abnormal (pseudo-high value) (step S66). Rules 1 to 4 are broadly divided into rules having lipid particles as the cause of abnormality (rules 1 and 2), and rules having poor hemolysis as the cause of abnormality (rules 3 and 4).

[Condition of Determining Abnormality Caused by Lipid Particles: Rule 1, Rule 2]

Determination on whether or not an abnormality caused by lipid particles is occurring is performed by determining whether or not lipid particles appear in the DIFF scattergram as the first measurement data or the WBC/BASO scattergram as the second measurement data. That is, a predetermined region for lipid particle detection is set in the scattergram, and determination is made on whether or not the lipid particles have appeared according to the number of particles etc. in the predetermined region.

In most cases, the lipid particles appear horizontally along the lower right in the scattergram of 4DIFF (first measurement), as shown in FIG. 10(a). That is, the lipid particle has lower fluorescence intensity (degree of staining) than the white blood cells (lymphocytes, monocytes, neutrophilic leucocytes, basophilic leucocytes, acidophilic leucocytes). In other words, the lipid particles have a fluorescence intensity of about the same extent as or lower than the red blood cell ghost. Furthermore, the lipid particles tend to be widely distributed from a range in which the lateral scattered light intensity (complexity of the inside of the particle) is low to the range in which the lateral scattered light intensity is high.

Therefore, the lipid particles appear mainly in the ghost region that is lower than the ghost/white blood cells boundary in the DIFF scattergram, whereby the number of white blood cells based on the DIFF scattergram barely contains number of lipid particles.

Figure 10B:
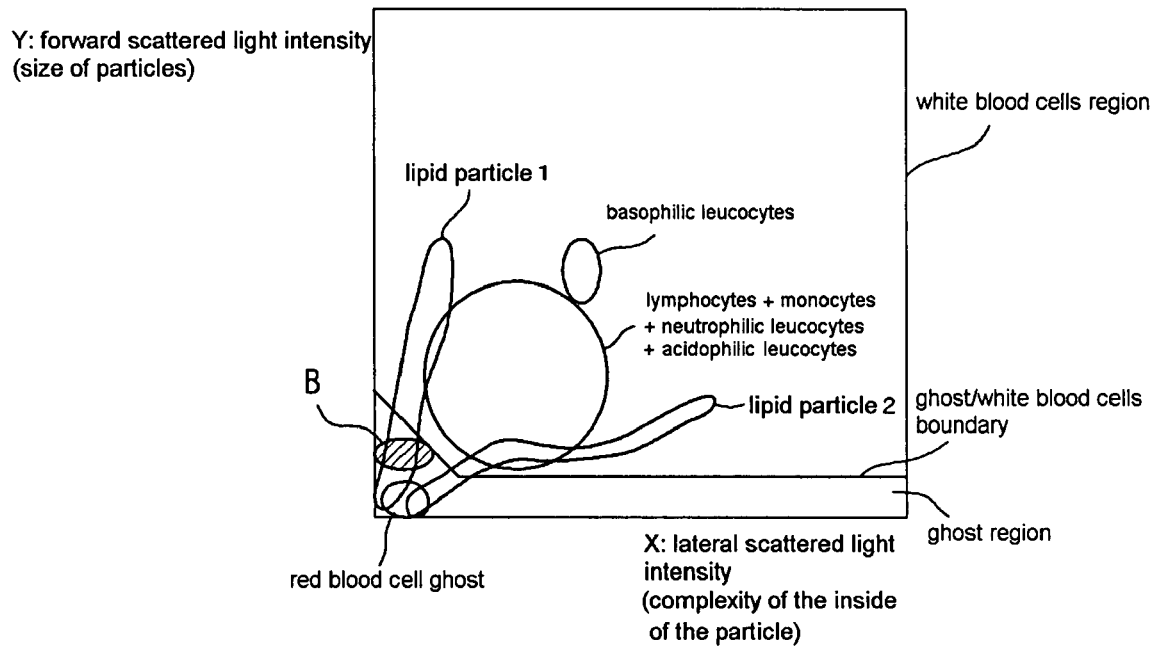
Figure 12A:
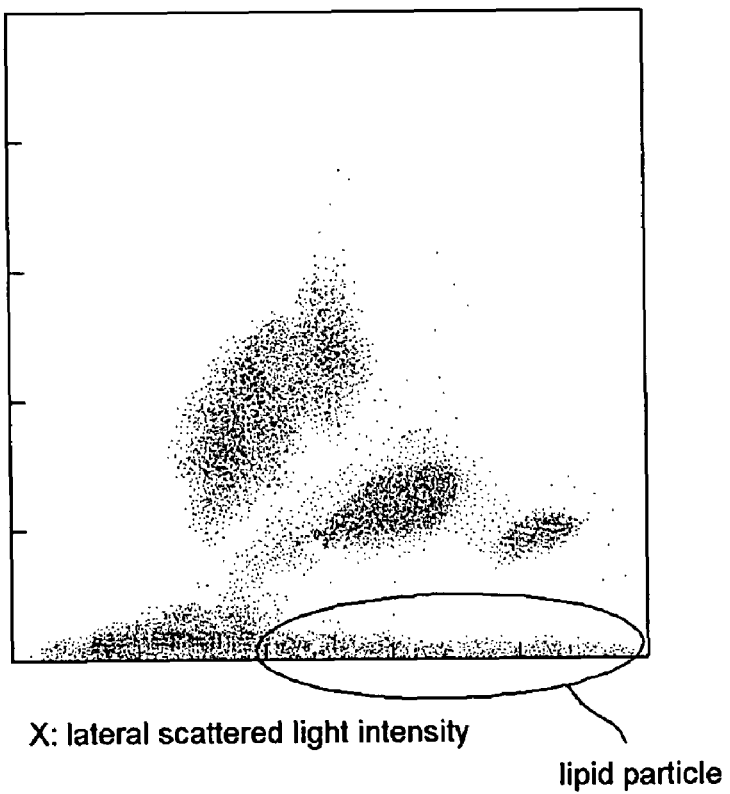
FIG. 12(a) and FIG. 12(b) are scattergrams in which the lipid particles have appeared.
Figure 12B:
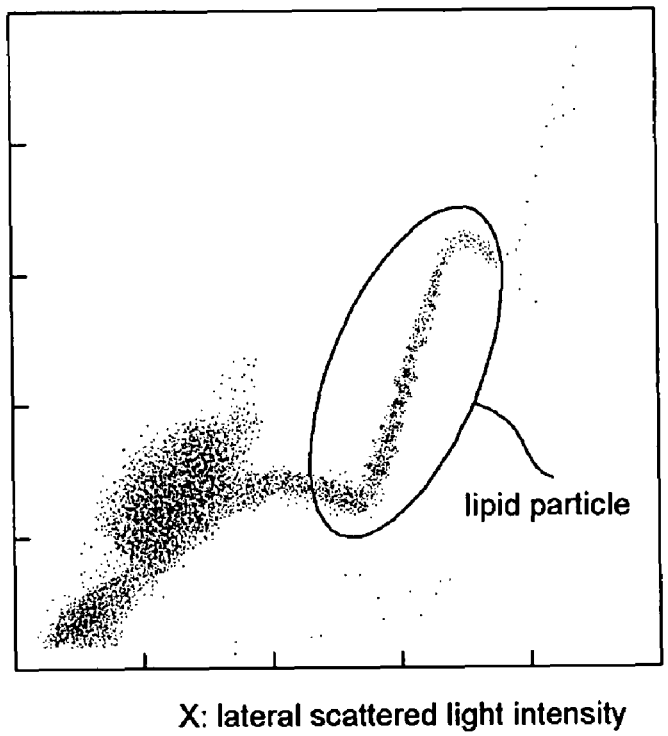

The lipid particles sometimes appear in a mustache form at positions indicated as "lipid particle 1" or "lipid particle 2" in the vicinity of the white blood cells (excluding basophilic leucocytes) group in the WBC/BASO (second measurement) scattergram, as shown in FIG. 10(b), but the location thereof is not necessarily constant as opposed to the DIFF scattergram. The "lipid particle 2" shown in FIG. 10(b) corresponds to the lipid particles shown in FIG. 12(b).

In either the lipid particle 1 or 2 positions, the lipid particles are also in the range of white blood cells above the ghost/white blood cells boundary in the WBC/BASO scattergram, and thus the number of white blood cells based on the WBC/BASO scattergram tends to contain a considerable number of lipid particles. Furthermore, even if a fractionating process is performed on the WBC/BASO scattergram, fractionation abnormality in which fractionation cannot be performed appropriately may occur, whereby the number of white blood cells obtained after the fractionating process also contains a considerable number of lipid particles.

[Rule 1]

In rule 1, the determination is identified as abnormal when a predetermined number of ghost particles are present in region A shown in FIG. 10(a).

Rule 1 uses the fact that the lipid particles appear at the bottom (ghost range) of the DIFF scattergram obtained by the first measurement (DIFF measurement), and is a rule targeting on the DIFF scattergram. That is, the lipid particle detection region A is set in the DIFF scattergram. Region A is set in the ghost range below the ghost/white blood cells boundary, but is a region where the red blood cell ghost normally does not appear although it is in the ghost range and is set at a position where the lipid particles sometimes appear.

Specifically, region A is set in a range (right side of red blood cell ghost in FIG. 10(a)) in which the lateral scattered light intensity is higher than the position where the group of red blood cell ghost normally appear (position of low lateral scattered light intensity) in the ghost range.

If the first measurement data corresponds to rule 1, determination is made that the lipid particles are present in the blood sample, and the number of white blood cells by the WBC/BASO measurement is a pseudo-high value.

Since the lipid particles also appear in the white blood cells range of the WBC/BASO scattergram (lipid particle 2 indicated in FIG. 10(b)), region A may be set in the white blood cells range of the WBC/BASO scattergram at a position distinguishable from the white blood cells.

[Rule 2]

In rule 2, the determination is identified as abnormal when a predetermined number of ghost particles are present in a region B indicated in FIG. 10(b).

Rule 2 uses the fact that "lipid particle 1" shown in FIG. 10(b) appears within the ghost range (lower range of ghost/white blood cells boundary) of the WBC/BASO scattergram obtained by the second measurement (WBC/BASO measurement), and is a rule targeting in the WBC/BASO scattergram. That is, region B is set on the WBC/BASO scattergram as the lipid particle detection region. Region B is set in the ghost range below the ghost/white blood cell boundary, but is set in a region where the red blood cell ghost normally do not appear although it is in the ghost range and at a position the lipid particles sometimes appear.

Specifically, region B is set in a range (upper side of red blood cell ghost) in which the forward scattered light intensity is higher than the position (position of low forward scattered light intensity) where the group of red blood cell ghost normally appear in the ghost range.

If the second measurement data corresponds to rule 2, determination is made that the lipid particles are present in the blood sample, and the number of white blood cells by the WBC/BASO measurement is a pseudo-high value.

Since the lipid particles also appear in the white blood cells range of the scattergram, the region B may be set in the white blood cells range of the scattergram at a position distinguishable from the white blood cells.

According to rules 1 and 2, "lipid particle 1" and "lipid particle 2" shown in FIG. 10(b) are both detectable. In particular, "lipid particle 1" and "lipid particle 2" are both detectable by rule 1. Specifically, the detection accuracy is high since "lipid particle 1" is also detectable by rule 2. Furthermore, rule 1 allows the lipid particles to be mostly detectable even when appeared at other positions shown in FIG. 10(b).

[Condition of Determining Abnormality Caused by Poor Hemolysis: Rule 3, Rule 4]

The determination on whether abnormality caused by poor hemolysis is occurring is performed by whether or not particles of poor hemolysis (red blood cells) have appeared in the WBC/BASO scattergram as the second measurement data. That is, determination is made on whether hemolysis is poor according to the number of particles etc. at a predetermined position in the WBC/BASO scattergram.

Figure 13A:
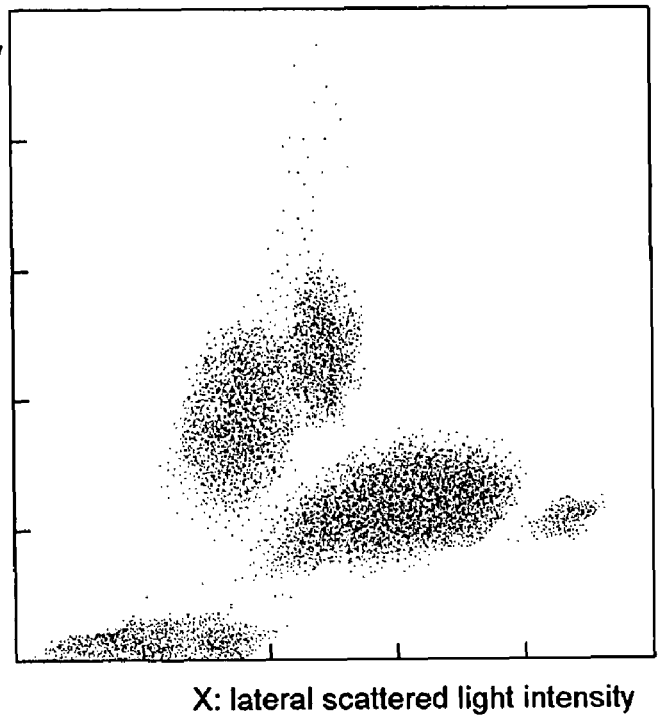
FIG. 13(a) and FIG. 13(b) are scattergrams in which particles of poor hemolysis have appeared.
Figure 13B:
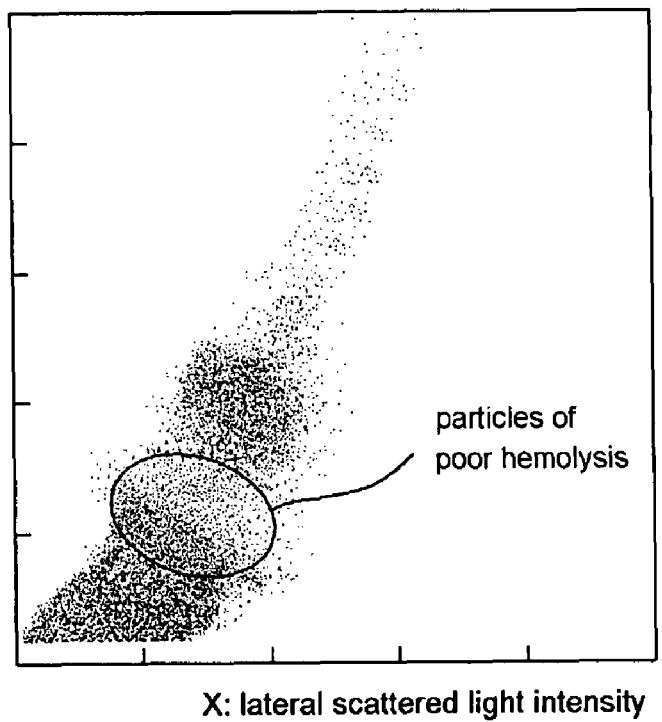
Figure 14A:
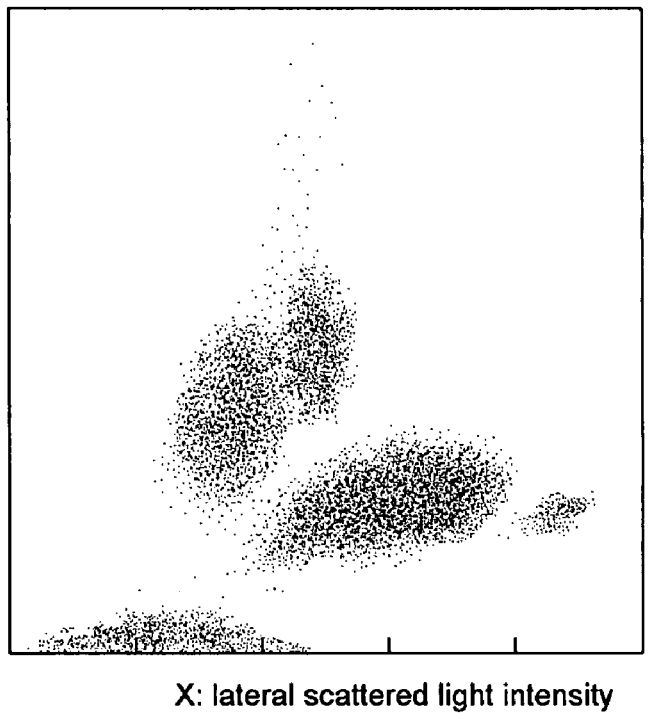
FIG. 14(a) and FIG. 14(b) are other scattergrams in which particles of poor hemolysis have appeared.
Figure 14B:
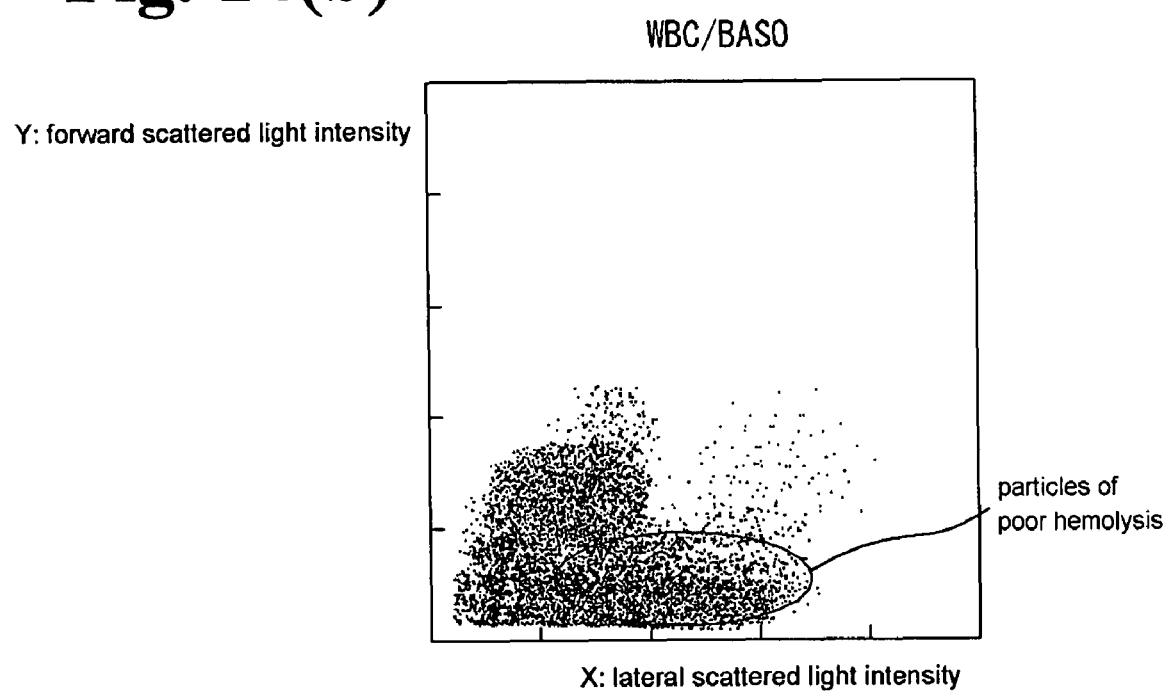

The particles of poor hemolysis appear at an intermediate position of the white blood cells cluster excluding the basophilic leucocytes and the red blood cell ghost cluster or on the right side (slightly lower right) from the intermediate position in the WBC/BASO scattergram (see FIG. 13(b) and FIG. 14(b)).

That is, the red blood cells of poor hemolysis appear over the boundary near the ghost/white blood cells boundary. In other words, the red blood cells of poor hemolysis appear between the boundary line of the white blood cells cluster and the boundary line of the red blood cell ghost cluster or in the vicinity of both boundary lines.

Generally, if particles of poor hemolysis are not present and thus is not abnormal, the number of particles is few at the intermediate position of the white blood cells cluster and the red blood cell ghost cluster, but the red blood cells that are not sufficiently hemolyzed are distributed at the intermediate position of the white blood cells cluster and the red blood cell ghost cluster or on the right side thereof if the red blood cells are poorly hemolyzed.

Therefore, the red blood cells of poor hemolysis also appear in the white blood cells range above the ghost/white blood cells boundary in the WBC/BASO scattergram, and thus the number of white blood cells based on the WBC/BASO scattergram contains considerable number of red blood cells of poor hemolysis.

On the other hand, the red blood cells of poor hemolysis appear mainly in the ghost range below the ghost/white blood cells boundary in the DIFF scattergram, and thus the number of white blood cells based on the DIFF scattergram barely contains number of red blood cells of poor hemolysis.

[Rule 3]

Figure 11:
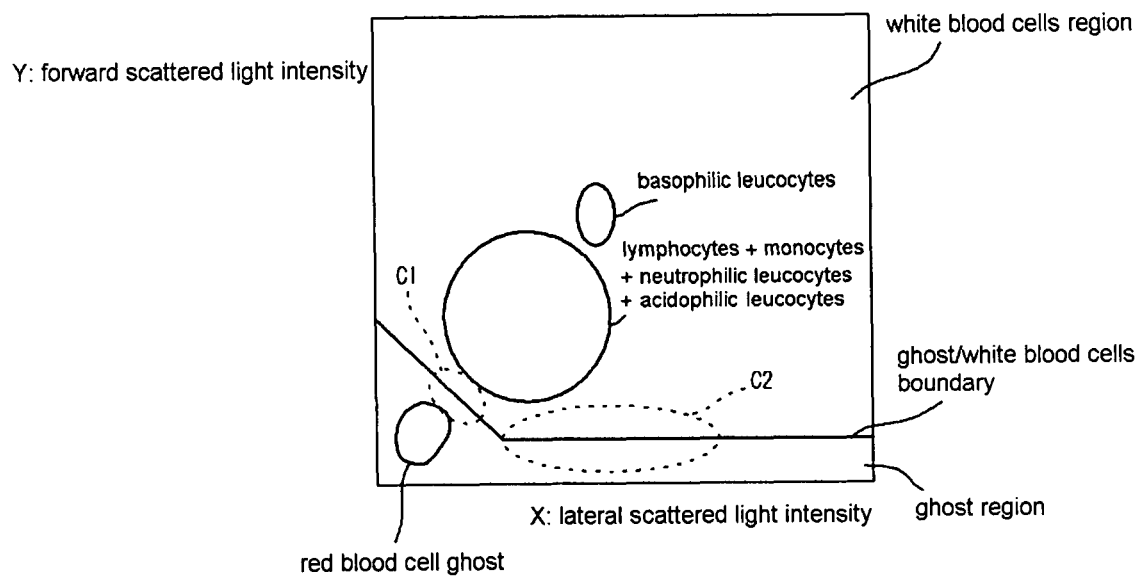
FIG. 11 is an explanatory view for detecting particles of poor hemolysis on the scattergram.

In rule 3, determination is identified as abnormal if a predetermined number of or greater number of particles is present at an intermediate position (first region near ghost/white blood cells boundary) C1 of the red blood cell ghost cluster and the white blood cells cluster excluding the basophilic leucocytes, as shown in FIG. 11.

If the second measurement data corresponds to rule 3, determination is made that the red blood cells of poor hemolysis are present in the blood sample, and the number of white blood cells by the WBC/BASO measurement is a pseudo-high value.

[Rule 4]

In rule 4, determination is identified as abnormal if a predetermined number or greater particles is present on the right side (second region near ghost/white blood cells boundary) C2 from the intermediate position of the red blood cell ghost cluster and the white blood cells cluster excluding the basophilic leucocytes, as shown in FIG. 11.

If the second measurement data corresponds to rule 4, determination is made that the red blood cells of poor hemolysis are present in the blood sample, and the number of white blood cells by the WBC/BASO measurement is a pseudo-high value.

[Switching in Display of Number of White Blood Cells]

The data processing unit 3 determines that switching in output of white blood cells is unnecessary, when the number of white blood cells is normal because measurement data obtained by the measuring unit 2 do not correspond to any one of the rules 1 to 4 (step S3-7), and outputs the number of white blood cells detected by the WBC/BASO measurement to the display (output section) 302, the printer, or the like (normal display: step S3-9). Meanwhile, when the number of white blood cells is abnormal in which measurement data obtained by the measuring unit 2 corresponds to one of the rules 1 to 4, the data processing unit 3 determines that switching in output of white blood cells is necessary (step S3-7), and outputs the number of white blood cells detected by the DIFF measurement (switched display; step S3-8).

When outputting the number of white blood cells detected by the DIFF measurement, it is displayed so that user is able to know that it is not the number of white blood cells detected by the WBC/BASO measurement. For instance, when outputting the number of white blood cells detected by the DIFF measurement, it is displayed with a special mark.

Therefore, according to the analyzer 1 of the present embodiment, the number of white blood cells of pseudo-high value which is caused by the lipid particles or the red blood cells of poor hemolysis is prevented from being displayed.

Furthermore, in the present embodiment, the analyzer 1 is configured to determine the abnormality of the number of white blood cells based on whether or not the lipid particles are contained in the particles recognized as the ghost particles other than the white blood cells. If lipid particles are present, distinction between the white blood cells and the lipid particles is not necessarily easy, and thus abnormality of the number of white blood cells can be determined in a relatively easy manner by determining whether or not the lipid particles are contained in the particles recognized as the ghost particles other than the white blood cells.

The present invention is not limited to the above embodiments, and various variants are possible. For instance, the particles that become the cause of pseudo-high value are not limited to lipid particles and red blood cells of poor hemolysis, and may be other particles.

Furthermore, when detecting the lipid particles, the white blood cells range (particularly, location where lipid particles appear in the white blood cells range of the WBC/BASO scattergram) may be given attention instead of the ghost range of the scattergram.

Furthermore, the distribution chart preparing part 64 may be provided in the data processing unit 3 instead of the measuring unit 2.

What is claimed is:

1. An apparatus which automatically counts a white blood cell in a blood sample, comprising:
    an output device; and
        a controller configured to perform operations comprising:
    obtaining a first white blood cell number by performing a first classification to classify white blood cells contained in a blood sample into at least four groups, and totaling a number of the white blood cells belong to the at least four groups, based on first measurement data obtained by measuring a first measurement sample prepared from the blood sample and a first reagent, the first measurement data having first and second optical information as parameters;
        obtaining a second white blood cell number by performing a second classification to classify white blood cells contained in the blood sample into basophils and other white blood cells, and totaling a number of the white blood cells belong to the basophils and the other white blood cells, based on second measurement data obtained by measuring a second measurement sample prepared from the blood sample and a second reagent different from the first reagent, the second measurement data having the second optical information and third optical information as parameters;
        determining whether the second white blood cell number includes a number of particles other than the white blood cells, based on at least one of the first measurement data and the second measurement data; and
        controlling the output device so as to output the first white blood cell number without outputting the second white blood cell number, when it has been determined that the second white blood cell number includes the number of the particles other than the white blood cells.

2. The apparatus of claim 1, wherein the controller is configured to classify the white blood cells in the blood sample into five groups, based on a first classification result obtained by the first classification and a second classification result obtained by the second classification.

3. The apparatus of claim 1, wherein the controller is configured to classify the white blood cells in the blood sample into monocytes, lymphocytes, a group of neutrophilic leucocytes and basophils and acidophilic leucocytes by the first classification.

4. The apparatus of claim 1, further comprising a detector for optically measuring the first and second measurement samples and detecting the first, second and third optical information.

5. The apparatus of claim 1, wherein the controller is configured to perform operations comprising:
    preparing a first distribution chart which represents a state of distribution of particles contained in the first measurement sample based on the first measurement data; and
    preparing a second distribution chart which represents a state of distribution of particles contained in the second measurement sample based on the second measurement data.

6. The apparatus of claim 1, wherein the particles other than the white blood cells comprise lipid particles contained in the second measurement sample.

7. The apparatus of claim 6, wherein the controller is configured to determine that the second white blood cell number includes the number of the lipid particles when the controller determines that the lipid particles are contained in particles recognized as ghost particles other than the white blood cells.

8. The apparatus of claim 1, wherein the particles other than the white blood cells are red blood cells caused by a poor hemolysis in the second measurement sample.

9. The apparatus of claim 8, wherein the controller is configured to determine whether the second white blood cell number includes the number of the red blood cells caused by the poor hemolysis, based on the second measurement data.

10. The apparatus of claim 9, wherein the controller is configured to determine whether the second white blood cell number includes the number of red blood cells caused by the poor hemolysis, based on a number of particles existing near a boundary which distinguishes the white blood cells from ghost particles other than the white blood cells in the second measurement data.

11. An apparatus which automatically counts a white blood cell in a blood sample, comprising:
    an output device; and
    a controller configured to perform operations comprising:
        obtaining a first white blood cell number by performing a first classification to classify white blood cells contained in a blood sample into at least four groups, and totaling a number of the white blood cells belong to the at least four groups, based on first measurement data obtained by measuring a first measurement sample prepared from the blood sample and a first reagent, the first measurement data having first and second optical information as parameters;
        obtaining a second white blood cell number by performing a second classification to classify white blood cells contained in the blood sample into basophils and other white blood cells, and totaling a number of the white blood cells belong to the basophils and the other white blood cells, based on second measurement data obtained by measuring a second measurement sample prepared from the blood sample and a second reagent different from the first reagent, the second measurement data having the second optical information and third optical information as parameters;
        determining whether the second white blood cell number includes a number of particles other than the white blood cells, based on at least one of the first measurement data and the second measurement data;
        selecting the first white blood cell number when it has been determined that the second white blood cell number includes the number of the particles other than the white blood cells, and selecting the second white blood cell number when it has been determined that the second white blood cell number does not include the number of the particles other than the white blood cells; and
        controlling the output device so as to output the selected number of the white blood cells.

12. The apparatus of claim 11,
    wherein the particles other than the white blood cells are lipid particles contained in the second measurement sample.

13. The apparatus of claim 11, wherein the particles other than the white blood cells are red blood cells caused by a poor hemolysis in the second measurement sample.

14. A method which automatically counts a white blood cell in a blood sample, comprising steps of:
    (a) performing a first classification to classify white blood cells contained in a blood sample into at least four groups based on first measurement data obtained by measuring a first measurement sample prepared from the blood sample and a first reagent, the first measurement data having first and second optical information as parameters;
    (b) totaling a number of the white blood cells belong to the at least four groups;
    (c) performing a second classification to classify white blood cells contained in the blood sample into basophils and other white blood cells, based on second measurement data obtained by measuring a second measurement sample prepared from the blood sample and a second reagent different from the first reagent, the second measurement data having the second optical information and third optical information as parameters;
    (d) totaling a number of the white blood cells belong to the basophils and the other white blood cells;
    (e) determining whether the number of the white blood cells obtained in the step (d) includes a number of particles other than the white blood cells, based on at least one of the first measurement data and the second measurement data; and
    (f) outputting the number of the white blood cells obtained in the step (b) without outputting the number of the white blood cells obtained in the step (d), when the number of white blood cells obtained in step (d) has been determined to include the number of the particles other than the white blood cells.

15. The method of claim 14, wherein the particles other than the white blood cells are lipid particles contained in the second measurement sample.

16. The method of claim 14, wherein the particles other than the white blood cells are red blood cells caused by a poor hemolysis in the second measurement sample.

17. The apparatus of claim 6, wherein the controller is configured to determine whether the second white blood cell number includes the number of the lipid particles, based on at least one of a number of particles appearing in a first area in the first measurement data and a number of particles appearing in a second area in the second measurement data, wherein the first area is different from an area where white blood cells appear in the first measurement data, and the second area is different from an area where white blood cells appear in the second measurement data.

* * * * *